United States Patent
Salo et al.

(10) Patent No.: US 6,217,512 B1
(45) Date of Patent: *Apr. 17, 2001

(54) SELF-ILLUMINATED, NON-INVASIVE, VISUAL CERVICAL INSPECTION APPARATUS AND METHOD

(75) Inventors: Timothy J. Salo; Theodore J. Colburn, both of Seattle, WA (US)

(73) Assignee: Program for Appropriate Technology in Health, Seattle, WA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/989,620

(22) Filed: Dec. 12, 1997

(51) Int. Cl.[7] .................................................. A61B 1/303
(52) U.S. Cl. ........................ 600/160; 600/135; 600/168; 600/179; 600/476
(58) Field of Search .................................. 600/184, 188, 600/190, 197, 199, 200, 210, 220, 223, 225, 235, 245, 249, 476, 477, 478, 160, 168, 177, 179, 130, 131, 129; 433/29; 359/385, 387, 798–803

(56) References Cited

U.S. PATENT DOCUMENTS

| | | | |
|---|---|---|---|
| 2,087,081 | * | 7/1937 | Bock . |
| 2,476,783 | * | 7/1949 | Turner et al. . |
| 3,090,379 | * | 5/1963 | Ferris et al. .......................... 600/179 |
| 3,605,730 | * | 9/1971 | Hotchkiss ............................ 600/200 |
| 3,840,004 | * | 10/1974 | Heine ................................... 600/200 |
| 3,910,701 | * | 10/1975 | Henderson et al. ................ 600/476 |
| 3,945,712 | * | 3/1976 | Crock et al. . |
| 4,195,918 | * | 4/1980 | Freche et al. ....................... 600/168 |
| 4,210,133 | * | 7/1980 | Castaneda ........................... 600/179 |
| 4,300,570 | * | 11/1981 | Stafl .................................... 600/476 |
| 4,491,131 | * | 1/1985 | Vassiliadis . |
| 4,528,986 | * | 7/1985 | Arundel et al. ...................... 600/476 |
| 5,014,707 | * | 5/1991 | Schwarz et al. ..................... 600/476 |
| 5,377,686 | * | 1/1995 | O'Rourke et al. .................. 600/476 |
| 5,421,339 | * | 6/1995 | Ramanujam et al. ............... 600/477 |
| 5,479,293 | * | 12/1995 | Reed .................................... 359/432 |
| 5,579,772 | * | 12/1996 | Kinukawa et al. .................. 600/476 |
| 5,644,438 | * | 7/1997 | Pottash ................................ 600/179 |
| 5,688,224 | * | 11/1997 | Forkey et al. ....................... 600/129 |
| 5,792,053 | * | 8/1998 | Skladnev et al. ............... 600/477 X |
| 5,851,181 | * | 12/1998 | Talmor ................................. 600/476 |
| 5,879,286 | * | 3/1999 | Krauter et al. ...................... 600/135 |
| 5,880,884 | * | 3/1999 | Hauptli ................................ 359/482 |
| 5,908,294 | * | 6/1999 | Schick et al. ......................... 433/29 |
| 5,986,271 | * | 11/1999 | Lazarev et al. .................. 250/458.1 |
| 5,989,184 | * | 11/1999 | Blair .................................... 600/109 |

* cited by examiner

Primary Examiner—John P. Leubecker
(74) Attorney, Agent, or Firm—Marger Johnson & McCollom, P.C.

(57) ABSTRACT

A visual cervical inspection apparatus for visual inspection of a cervix has a housing having a cavity. The housing has a proximal viewing aperture located in a proximal end of the housing and a distal aperture at a distal end of the housing. A light source is attached to the housing and is adapted to illuminate the cervix with light sufficient to visibly enhance the definition between cancerous and healthy cervical tissue. Magnification optics are disposed within the cavity of the housing which provide for magnified viewing of the illuminated cervix. The visibly enhanced definition between cancerous and healthy cervical tissue can thus be more easily viewed by a user of the visual cervical inspection apparatus. Light emitting diodes of the appropriate light wavelength can be used to provide the necessary illumination of the cervix. Krypton, xenon or other similar bulbs may also be used when filtered to produce light of approximately between 480–580 nanometers.

20 Claims, 4 Drawing Sheets

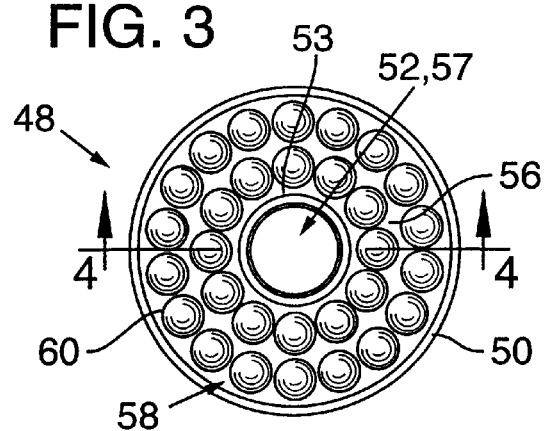
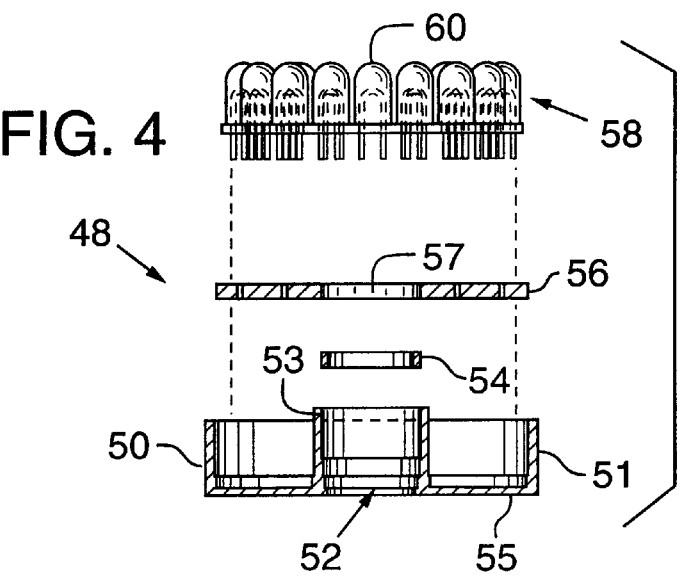
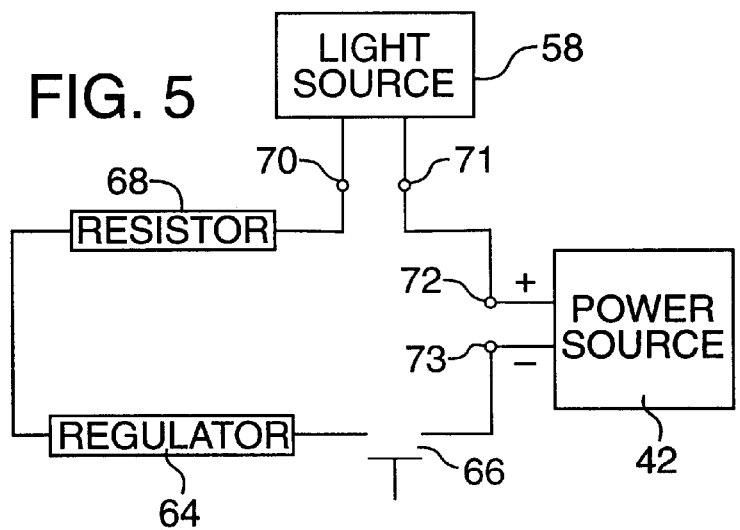

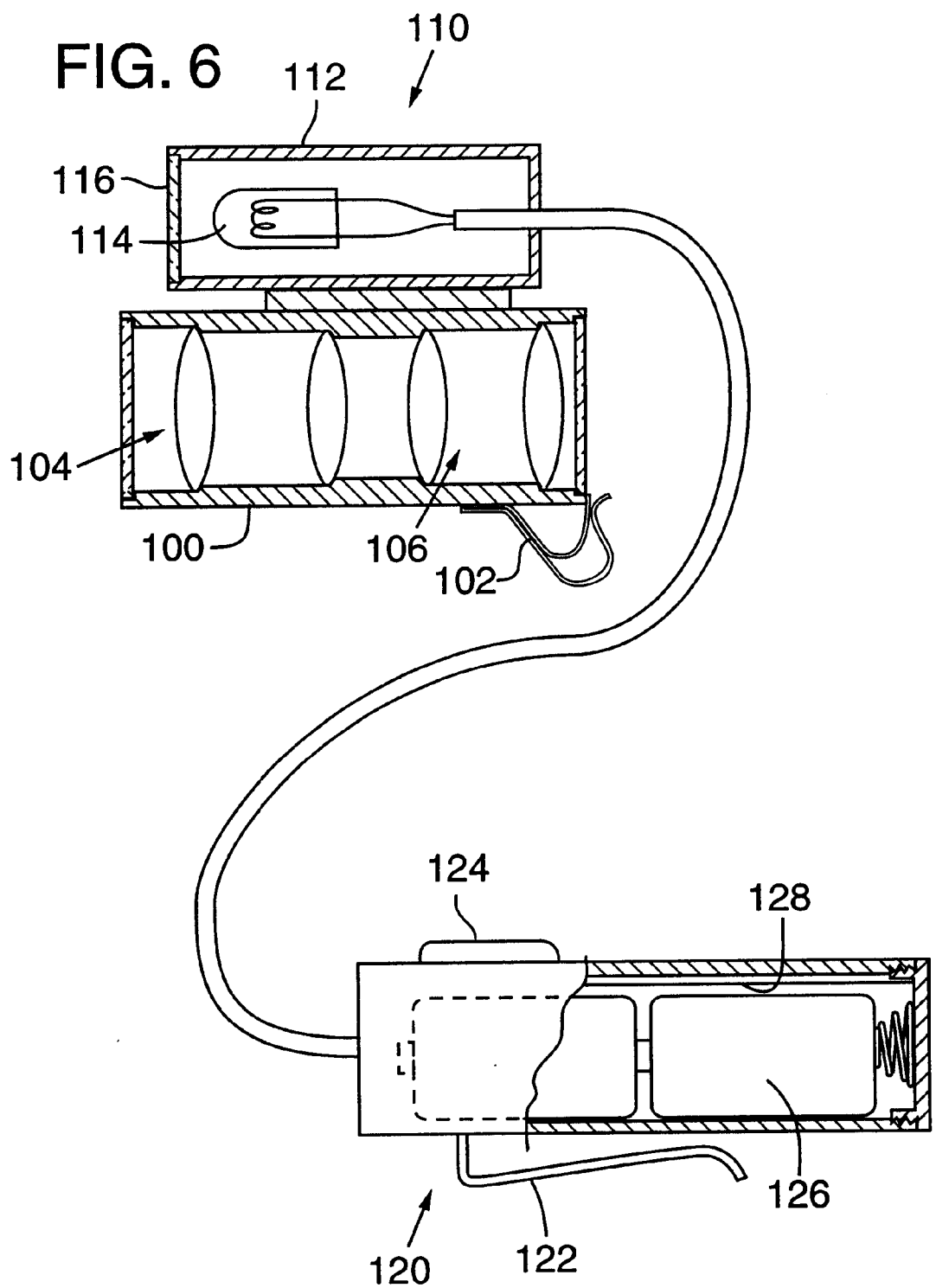

SELF-ILLUMINATED, NON-INVASIVE, VISUAL CERVICAL INSPECTION APPARATUS AND METHOD

The U.S. Government has a paid-up license in this invention and the right in limited circumstances to require the patent owner to license others on reasonable terms as provided for by the terms of contract No. 2 R44 CA65313-02A1 awarded by the National Institutes of Health.

BACKGROUND OF THE INVENTION

This invention relates generally to medical devices and methods for identifying diseased tissue. More particularly, this invention relates to a cervical inspection apparatus providing magnification for visually detecting various degrees of cervical dysplasia or carcinoma in situ.

Conventionally, cervical inspection has been done primarily by taking cell samples during Papanicolaou (Pap) smear visits. The cell samples thus taken are sent to a laboratory and diagnosed to determine whether or not there is any abnormality or cancerous growth in the cervical tissue. Pap smear test are still, by far, the most commonly used cervical inspection method.

More recently, however, methods and devices have been developed for the visual inspection of the cervix. These visual inspection techniques and devices generally involve an initial treatment of the cervix with an acetic acid solution and a subsequent inspection of the cervix either with the unaided eye or with the help of a low-powered magnification device. Lighting for conventional visual inspection techniques is provided by a separate, external light source. Visual inspection with the aid of a low-powered magnification device and appropriate lighting has been proven in clinical trials to be successful in detecting moderate to severe dysplasia (CIN II and III) with a fair degree of sensitivity and specificity.

One particular prior art visual inspection method involves the use of a chemilucent tube attached to the end of a speculum and inserted into an acetic acid treated cervix to provide the required lighting. A separate binocular magnification device is used to inspect the cervix, as illuminated by the chemically created light. The chemilucent light is of a wavelength such that the differences between the normal and diseased cervical tissue can be distinguished, typically within the green spectrum.

A related prior art visual inspection method involves the use of a high-powered halogen light in combination with fiber-optic tubing for providing the appropriate lighting. Fiber-optic tubing of an appropriate hue is attached to a speculum and inserted into the cervix. The tubing is illuminated using a high-powered halogen lamp, and the cervix is then inspected using a low-powered magnification device, as in the other prior art, discussed previously.

Other prior art visual inspection methods include use of a high-powered lamp of the appropriate hue, or with an appropriate light filter to provide adequate lighting, and visual inspection of the cervix with either a separate magnification device or the unaided eye.

Despite the widespread need for accurate cervical inspection, there are a number of severe limitations to each of the prior art cervical inspection methods and/or devices. Initially, although pap smear tests are substantially accurate in determining cervical health, they do not yield immediate results, are invasive, and are fairly expensive to obtain. The test samples obtained by this invasive, hence uncomfortable, method must be sent to a lab for diagnosis and even when a lab is readily available, this process may take several weeks to complete. When labs are farther away or unavailable altogether, pap smear tests become impossible or, at least, completely impractical. Furthermore, pap smear tests require a setting that has available all the necessary equipment for taking and analyzing cervical cell samples, thus creating significant expense.

Visual inspection with the unaided eye, while readily available, inexpensive and capable of offering immediate results, is highly inaccurate and therefore the results obtained are inconsistent, and unreliable. Visual inspection without proper magnification is, for the most part, incapable of detecting moderate cases of dysplasia and even some severe cases. This method, therefore, is incapable of giving the desired and necessary level of precision. Furthermore, in order to be even minimally effective, unaided visual inspection still requires an optimal lighting condition that may be difficult to obtain, particularly in third-world countries or in rural areas of the United States and other countries.

Visual inspection with the aid of a magnification device is much more effective than unaided visual inspection in identifying unhealthy cervical tissue; however, this too requires an optimal lighting condition. High-powered lighting, as used in some of the prior art methods, is not available in many areas of the world, and hence those techniques are unavailable. In addition, traditional magnification devices are expensive (between $80–100US) and therefore do not provide a legitimate alternative for poorer regions of the world. Furthermore, the prior art visual inspection methods which do not require separate high-powered lighting are invasive and expensive. The chemilucent and fiber-optic tubes of the prior art are attached to the speculum and inserted into the cervix. These methods are therefore invasive, and uncomfortable for the patient, in practice. The chemilucent tubes further create a self-depleting light source having a limited life span. In addition, because both the chemilucent tubes and fiberoptic tubes are invasive, they are not safely reusable. These tubes therefore require replacement after every use and are expensive (about $6US each for the chemilucent tubes). Additionally, the halogen light used to illuminate the fiber-optic tubing should be high-powered to be effective and will therefore be impractical or unavailable in many settings where cervical inspection is needed.

A substantial need therefore exists in the industry for a cost-effective, non-invasive, cervical inspection apparatus and method capable of yielding immediate results with substantial accuracy, and further capable of being performed in areas with limited lighting capabilities or lacking modern hospital facilities or laboratories.

SUMMARY OF THE INVENTION

According to the described needs in the industry, one object of the present invention is to provide a cost-effective cervical inspection apparatus and method.

It is another object of this invention to provide a non-invasive cervical inspection apparatus and method.

It is a further object of this invention to enable a cervical inspection device to be used in areas with inadequate lighting.

Yet another object of this invention is to enable immediate, reliable, and cost-effective cervical inspection results, with a high degree of precision.

A further object of this invention is to enable cervical inspection, suitable in terms of both cost-efficiency, reliability, and apparatus design, to be used in third-world countries or poor or undeveloped areas.

In satisfaction of the foregoing objects, the present invention offers a significant advancement in the art of cervical inspection methods and devices by supplying a visual cervical inspection apparatus comprising a housing having a cavity defined therein, the cavity including a proximal viewing aperture in a proximal end of the housing and a distal aperture at a distal end of the housing. A light source is attached to the housing and adapted to illuminate the cervix with light sufficient to visibly enhance the definition between cancerous and healthy cervical tissue. Also, magnification optics are disposed within the cavity of the housing and adapted to permit magnified viewing of the illuminated cervix through the proximal viewing and distal apertures of the housing so that the visibly enhanced definition between cancerous and healthy cervical tissue can be more easily identified.

The foregoing and other objects, features and advantages of the invention will become more readily apparent from the following detailed description of a preferred embodiment of the invention which proceeds with reference to the accompanying drawings.

BRIEF DESCRIPTION OF THE DRAWINGS

FIG. 3 is a top plan view of a light source housing and LEDs of the visual cervical inspection apparatus of FIG. 1.

FIG. 4 is an enlarged, exploded, sectional view of the light source housing and LEDs, taken along line 4—4 in FIG. 3.

FIG. 5 is a schematic circuit diagram of a power source electronic circuit board for controlling a light source of the visual cervical inspection apparatus of FIG. 1.

FIG. 6 is a perspective view of a visual cervical inspection apparatus constructed according to a second preferred embodiment of the present invention.

DETAILED DESCRIPTION OF THE PREFERRED EMBODIMENT

Figure 1:
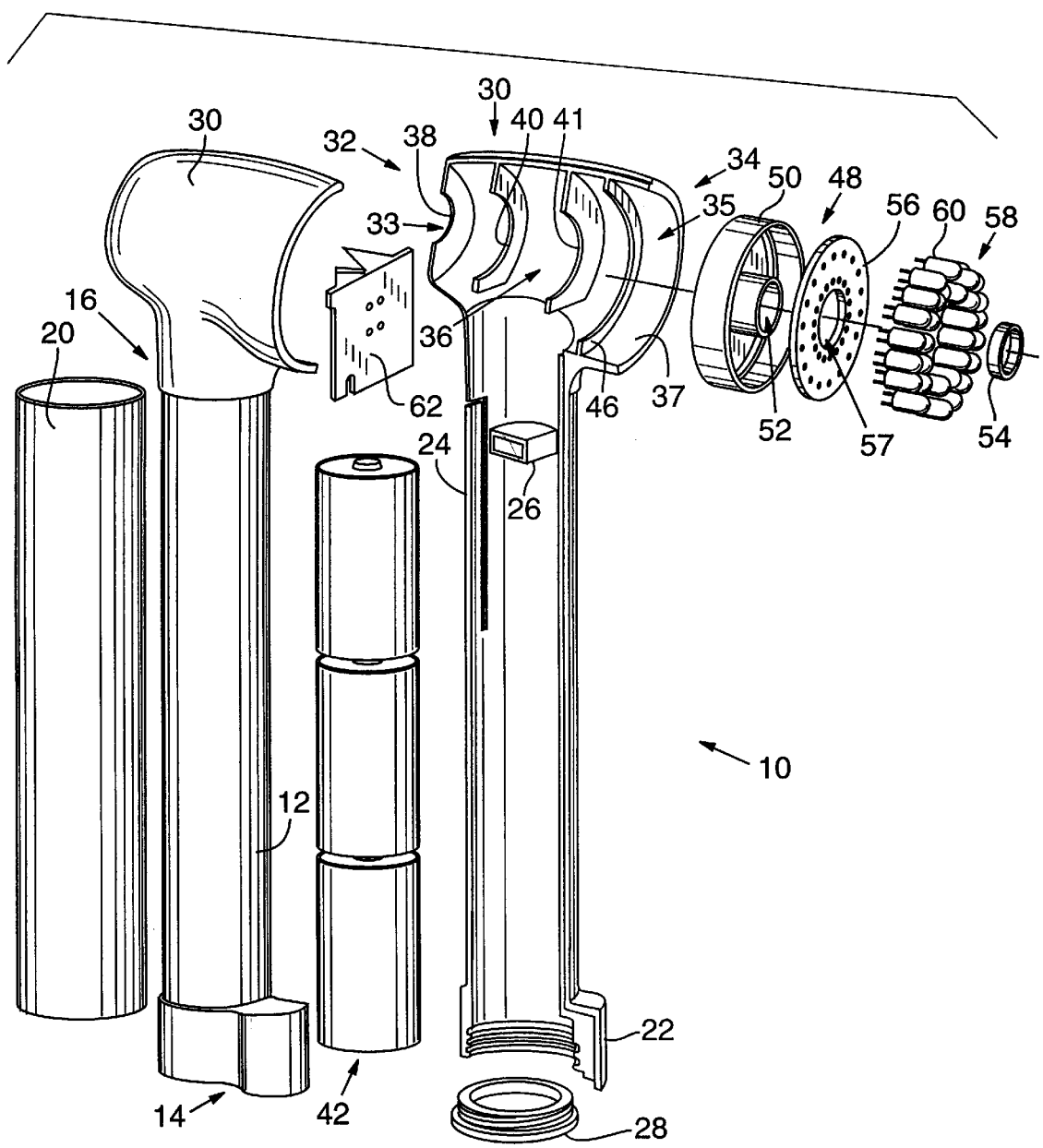
FIG. 1 is an exploded perspective view of a visual cervical inspection apparatus constructed according to a first preferred embodiment of the present invention.

Referring to FIG. 1, a first preferred embodiment of a visual cervical inspection apparatus according to the invention comprises a housing 10 that includes an integrally molded handle 12 and head portion 30. The handle 12 is shaped as a hollow cylinder with a cap 28 at an open distal end 14, to removably contain a power source 42. A rubber hand grip 20 may be placed around the handle 12 to provide a comfortable and slip resistant gripping surface. The head 30 comprises a hollow cavity 36, a proximal end 32 having a proximal viewing aperture 33, and a distal end 34 having a distal aperture 35. The distal end 34 of head 30 contains a light source housing 48, positioned against a stop 46, within the distal aperture 35. The light source housing 48 contains a light source circuit board 56 to which a light source 58 (comprising LEDs 60, in this embodiment) is attached. A power source circuit board 62 is located within the proximal end 16 of the handle 12 near the head 30 to regulate a current and a voltage conveyed from the power source 42 to the light source 58.

Figure 2:
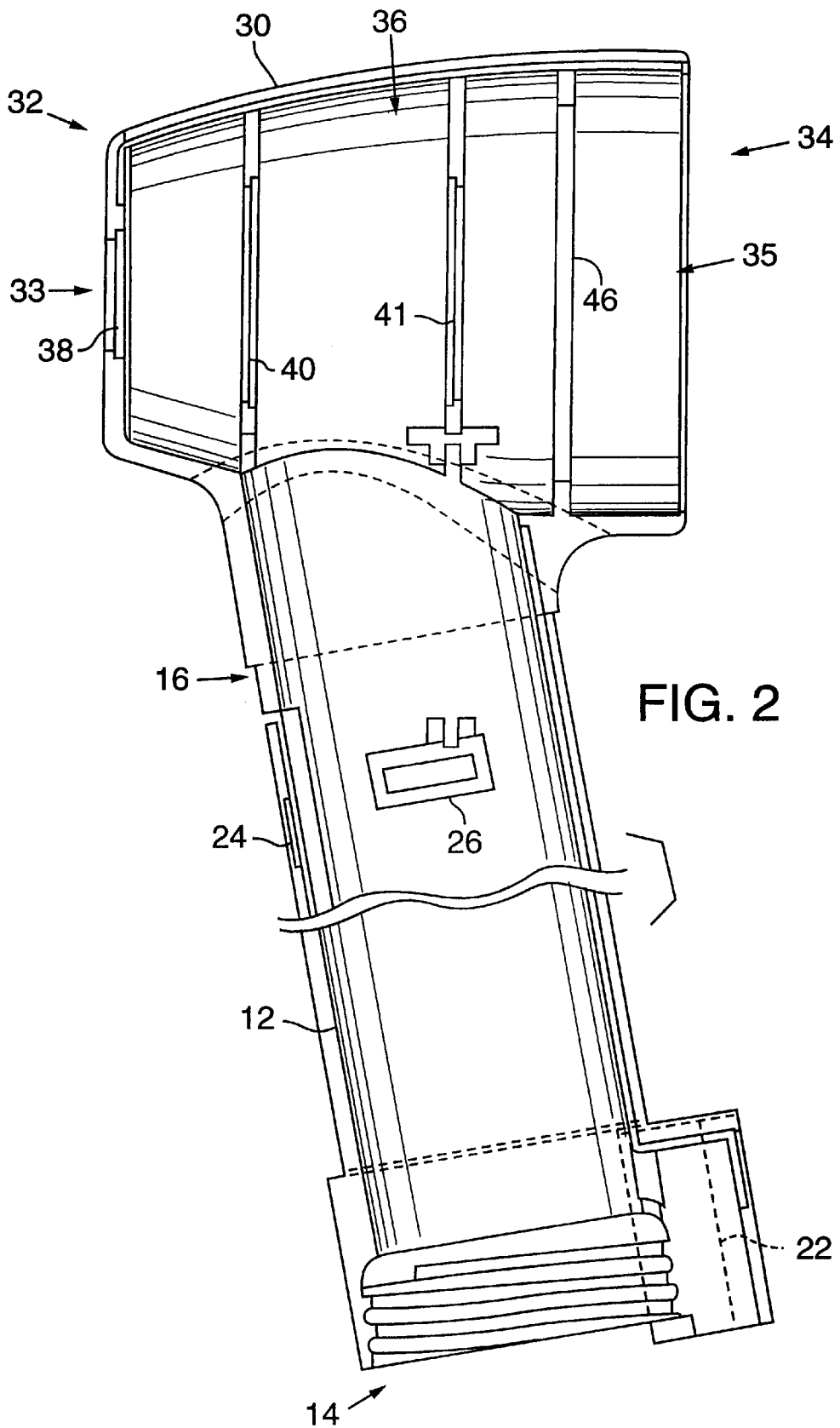
FIG. 2 is a half shell side view of the visual cervical inspection apparatus of FIG. 1.

Referring to FIGS. 1 and 2, an actuating lever 24 is located along the periphery of the handle 12, for actuating the light source 58. The power source 42, preferably comprised of three rechargeable "C" type batteries, fits within the handle 12. Contacting plate 26 and a spring (not shown) are located within the handle 12 and on cap 28, respectively, to contact a positive and a negative end of the power source 42, respectively. The actuating lever 24 is constructed and located such that depression of the actuating lever 24 activates a power switch 66 (see FIG. 5) of the power source circuit board 62, thus closing the circuit between the power source 42 and the light source 58, and actuating the light source 58. Cap 28 screws into the open distal end 14 of the handle 12 to removably contain the power source 42. The handle 12 also comprises a recharger connector enclosure 22 near the open distal end 14, which comprises an opening to communicate with a recharger base (not shown). The recharger base may be provided to recharge the power source 42 when the distal end 14 of the handle 12 is placed into the recharger base.

Further referring to FIG. 2, the head 30 comprises a cavity 36 and internal slot members 38, 40 and 41 for rigidly containing four lenses (not shown), providing the necessary magnification optics. A proximal viewing aperture 33, is located centrally on a face (not shown) of the proximal end 32 of the head 30. The distal aperture 35 of the distal end 34 of the head 30 accepts the light source housing 48. The stop 46 is located within the cavity 36 of the head 30 near the distal end 34 for positioning the housing 50 at an appropriate depth within the head 30.

In order to adequately view and diagnose the cervical tissue, the preferred magnification provided by the magnification optics of the cervical inspection apparatus is approximately 3×–8×, and most preferably 4×. The preferred focal length is approximately 10–15 inches, and most preferably about 13 inches (i.e. corresponding to a preferred distance between the distal end 34 of the head 30 and the illuminated cervix (not shown)). In order to obtain the preferred magnification at the preferred focal range, a lens system is provided which employs 4 lenses in series. The lens nearest the proximal end 34 of head 30, located in slot 38, is preferably a dual achromat objective lens consisting of a double convex and concave convex BK7-SF5 pair with a broadband multi-layer dielectric coating. The lens second from the proximal end 34, located in slot 40, is preferably a roof prism for image inversion with a broadband multi-layer dielectric coating on entrance surfaces of the lens. The other two lenses in the preferred embodiment are located together in slot 41 and comprise a wide field design eye lens assembly having two piano convex achromat lenses in an infinite conjugate geometry, each having a multi-layer dielectric coating.

Referring to FIGS. 3 and 4, the light source housing 48 of the first preferred embodiment of the present invention comprises a body 50 having a circular shape and a substantially planar bottom 55, with an external ridge 51 extending along the periphery of the body to frictionally fit within the distal aperture 35 of the distal end 34 of the head 30 (see FIG. 1). The body 50 further comprises a viewing aperture 52 located within the center of the bottom 55 of the body 50 and surrounded by an inner ridge 53. The light source circuit board 56 rests within external ridge 51 and contains a hole member 57 for communicating with the inner ridge 53. A ring 54 fits within the inner ridge 53.

The light source 58 of this preferred embodiment comprises a plurality of light emitting diodes (LEDs) 60 such as are commonly used in many electronic devices. The LEDs 60 are disposed in an array about the hole member 57 on the light source circuit board 56. The LEDs 60 emit visible light, preferably in the green wavelength band between approximately 480–580 nanometers (with about 560 nanometers being the most preferred wavelength). This wavelength has been found to produce the most visible contrast between healthy and unhealthy acetic acid treated cervical tissue. Though white light can be used to illuminate the inspected cervical tissue, such light tends to "wash out" the target area and, therefore, tends to reduce the contrast needed to diagnose the cancerous tissue.

The LEDs 60 preferably have about an eight (8) degree diffusion pattern. Their angular positions relative to the head 30 are therefore adjusted such that they appropriately illuminate an approximately 2 inch diameter focal area at a distance of approximately 13–15 inches. Once the LEDs 60 have been appropriately positioned, a potting material such as epoxy is introduced around the LEDs 60 which hardens to rigidly hold the LEDs 60 in an appropriate orientation on the light source circuit board 56. Other embodiments may comprise an original light source of a single or multiple xenon, krypton or other bulbs and a light filter to produce light of the appropriate wavelength. The bulbs may be located externally along the outer periphery of the head (see FIG. 6) or may be positioned within the housing cavity, similar to the LEDs of the first preferred embodiment.

Referring to FIG. 5, the power source circuit board 62 comprises a circuit for activation and regulation of the light source 58 using electricity supplied from the power source 42. The circuit board comprises a power regulator 64, a power switch 66, light source leads 70 and 71, and a positive and a negative input line 72 and 73, respectively, for receiving electricity from the power source 42. A resistor 68 (preferably 10 KΩ) can also be included, but is not required. The power source circuit board 62 functions to send the appropriate current and voltage to the light source 58 from the power source 42, when the power switch 66 is depressed. In operation, depression of the activating lever 24 of the handle 12 (see FIG. 1) closes the power switch 66, thereby closing the circuit on the power source circuit board 62. Once the circuit is closed, electricity from the power source 42 travels through the regulator 64 and the resistor 68 (if present) and activates the light source 58. The regulator 64 ensures that an appropriate power level is communicated to the light source 58, thereby providing the appropriate lighting level.

Referring to FIG. 6, a second preferred embodiment of a visual cervical inspection apparatus according to the present invention comprises a housing 100. A light source member 110 having an original light source of single or multiple xenon, krypton or similar bulb(s) 114, within a light source housing 112, is mounted along an outside of the housing 100 and provides light for inspection of the cervix. The light is filtered through a light filter 116 to provide for illumination of the cervix with the desired wavelength of light. The housing 100 comprises a cavity 106 for containing magnification optics 104 (shown schematically) and a clip 102 for clipping to an operator's glasses (not shown). The magnification optics 104 are similar to those of the previous embodiment. A power source unit 120 is located separate from the housing 100 and the light source member 110, and has a clip 122 so as to be worn on a pocket or belt of an operator. The power source unit 120 also has a button 124 to activate a switch on the power source circuit board 128 (similar to the power source circuit board shown in FIG. 5), thereby drawing electricity from the power source 126 to power the light source member 110.

Having described and illustrated the principles of the invention in a first and second preferred embodiment and other potential embodiments thereof, it should be apparent that the invention can be modified in arrangement and detail by those skilled in the art without departing from such principles. I, therefore, claim all modifications and variations coming within the spirit and scope of the following claims.

We claim:

1. A visual cervical inspection apparatus for external visual inspection and immediate, reliable diagnosis of a cervix, the visual cervical inspection apparatus comprising:
    a housing having a viewing cavity defined therein, said viewing cavity comprising a proximal viewing aperture in a proximal end of the housing and a distal aperture in a distal end of the housing, and further comprising a central axis extending along a center of the viewing cavity from the proximal end to the distal end;
    a light source attached to said housing and adapted to illuminate the cervix with light of a selected wavelength range sufficient to visibly enhance the definition between cancerous and healthy cervical tissue; and
    said housing consisting essentially of monocular magnification optics disposed within the viewing cavity of the housing along an optical path extending from the proximal viewing aperture to the distal aperture, said magnification optics adapted to permit direct magnified viewing of the cervix through the magnification optics so that the visibly enhanced definition between cancerous and healthy cervical tissue can be directly viewed by a user of the visual cervical inspection apparatus to permit immediate diagnosis of the cervix, said magnification optics adjusted to focus at a focal area approximately 10–15 inches from the distal end of said housing.

2. The visual cervical inspection apparatus of claim 1 further comprising a handle comprising a battery chamber, said handle attached to said housing and extending therefrom in a direction substantially transverse to the central axis of the viewing cavity.

3. The visual cervical inspection apparatus of claim 2, in which the handle is substantially cylindrical and wherein the battery chamber is sized to contain one or more C-type batteries.

4. The visual cervical inspection apparatus of claim 1 wherein the selected wavelength range is between approximately 480–580 nanometers.

5. The visual cervical inspection apparatus of claim 4, wherein the light source emits light primarily of a wavelength of approximately 560 nanometers.

6. The visual cervical inspection apparatus of claim 1, wherein the light source includes an original light source and a light filter coupled to the original light source for passing only light of the selected wavelength range to the cervix.

7. The visual cervical inspection apparatus according to claim 6, in which the light source comprises a xenon bulb and a light filter for producing light of a wavelength of about 480–580 nanometers.

8. The visual cervical inspection apparatus according to claim 6, in which the light source comprises a krypton bulb and a light filter for producing light of a wavelength of approximately between 480–580 nanometers.

9. The visual cervical inspection apparatus of claim 1, further including:
    a handle attached to the housing and oriented in a direction substantially transverse to the central axis of the viewing cavity; and
    means disposed within the handle for powering the light source.

10. The visual cervical inspection apparatus of claim 1, wherein the magnification optics comprises a four lens system having a fixed focal length.

11. The visual cervical inspection apparatus of claim 1, wherein the magnification optics has a magnification power of between about 3×–8×.

12. The visual cervical inspection apparatus of claim 1, wherein said light source is attached to an outside of the housing.

13. The visual cervical inspection apparatus according to claim 1, wherein said light source comprises a plurality of light emitting diodes.

14. The visual cervical inspection apparatus of claim 13, wherein said light emitting diodes are spaced in an array about the distal viewing aperture.

15. The visual cervical inspection apparatus according to claim 1, in which the light source is attached to the distal end of said housing and comprises a plurality of light emitting diodes arranged to focus light at a distance of about 13–15 inches from the distal end of the housing within a focal area having about a 2 inch diameter.

16. The visual cervical inspection apparatus according to claim 1, in which the visual cervical inspection apparatus further comprises:

a light source housing connected to and readily removable from the housing of the cervical inspection apparatus; and a light source circuit board retained within the light source housing, wherein the light source communicates with the light source circuit board.

17. The visual cervical inspection apparatus according to claim 16, in which the light source comprises a plurality of light emitting diodes.

18. A method for non-invasively visually inspecting and immediately diagnosing a cervix comprising:

treating the cervix with acetic acid;

non-invasively illuminating the cervix with a light source attached to a visual cervical inspection apparatus, said light source producing light having a wavelength of between about 480–580 nanometers;

directly viewing the cervix through monocular magnification optics located in the visual cervical inspection apparatus and immediately diagnosing a condition of the cervix based upon the direct viewing of the cervix.

19. The method for non-invasively visually inspecting and immediately diagnosing a cervix according to claim 18, further comprising:

focusing the magnification optics at a focal distance of approximately 10–15 inches from a distal end of the visual cervical inspection apparatus.

20. A visual cervical inspection apparatus for non-invasive visual inspection and immediate diagnosis of a cervix, the visual cervical inspection apparatus comprising:

a housing having a viewing cavity defined therein, said housing including a proximal viewing aperture in a proximal end of the housing and a distal aperture in a distal end of the housing;

magnification optics disposed within the viewing cavity of the housing along a viewing axis extending from the proximal viewing aperture to the distal aperture, said magnification optics adapted to permit direct magnified viewing of the cervix through the proximal viewing aperture;

a handle comprising a battery chamber, said handle attached to the housing and extending from the housing substantially transverse to the viewing axis; and a light source attached to a distal end of the housing and adapted to illuminate the cervix with light of a selected wavelength range sufficient to visibly enhance the definition between cancerous and healthy cervical tissue.

* * * * *